United States Patent
Strom et al.

(10) Patent No.: US 7,091,185 B2
(45) Date of Patent: Aug. 15, 2006

(54) PERIODIC ANTIMICROBIAL PEPTIDES

(75) Inventors: Robert M. Strom, Midland, MI (US); Philip J. Brondsema, Midland, MI (US)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/785,210

(22) Filed: Feb. 24, 2004

(65) Prior Publication Data

US 2005/0187151 A1      Aug. 25, 2005

Related U.S. Application Data

(60) Provisional application No. 60/560,737, filed on Feb. 24, 2003.

(51) Int. Cl.
*A61K 38/00* (2006.01)
*C07K 7/00* (2006.01)

(52) U.S. Cl. .......... 514/18; 514/19; 530/324; 530/325; 530/326; 530/327; 530/328; 530/329; 530/330

(58) Field of Classification Search .......... 514/18, 514/19
See application file for complete search history.

(56) References Cited

U.S. PATENT DOCUMENTS

| | | | |
|---|---|---|---|
| 5,114,921 A | 5/1992 | Zasloff | 514/12 |
| 5,789,384 A | 8/1998 | Khavinson et al. | 514/19 |
| 5,789,542 A | 8/1998 | McLaughlin et al. | 530/326 |
| 5,856,435 A | 1/1999 | Bazile et al. | 530/500 |
| 6,448,391 B1 | 9/2002 | Garbarino et al. | 536/24.1 |
| 6,531,446 B1 | 3/2003 | Kim et al. | 514/2 |

OTHER PUBLICATIONS

Chen et al., American Jounral of Veterinary Research, 2003, 64(9), 1088-92.*
Seipke et al., International Journal of Biological Macromolecules, 1980, 2(4), pp. 268-270.*
Durell SR, et al., "Modeling the ion channel structure of cecropin", Biophys J., Dec., 1992 63(6):1623-31.
E. Gazit, et al., Interaction of the Mammalian Antibacterial Peptide Cecropin P1 with Phospholipid Vesicles, Biochemistry, 1995, 34:11479.
Arlotti et al., Efficacy of a synthetic lytic peptide in the treatment of prostate cancer, Urol Oncol., 2001, 6(3): 97-102.
Javadpour, et al., De Novo Antimicrobial Peptides with Low Mammalian Cell Toxicity, J. Med. Chem., 1996, 39(16): 3107-3113.
Wachinger, et al., "Antimicrobial peptides melittin and cecropin inhibit replication of human immunodeficiency virus 1 by suppressing viral gene expression", J.Gen. Virol., 1998, (79): 731-740.
Jia Ma, et al., "Inhibitory Activity of Synthetic Peptide Antibiotics on Feline Immunodeficiency Virus Infectivity In Vitro", J. Virol., 2002, 76(19): 9952-9961.
S.E. Blondelle and Karl Lohner, "Biopolymers (Peptide Science)", 2000, vol. 55, 74-87.
Niidome et al., Required Structure of Cationic Peptide for Oligonucleotide-Binding and Delivering Into Cells, 2000, Journal of Peptide Science, vol. 6, No. 6, pp. 271-279.

* cited by examiner

Primary Examiner—Robert A. Wax
Assistant Examiner—Suzanne M. Noakes

(57) ABSTRACT

One embodiment of the invention comprises a method of producing periodic peptides, which can have antimicrobial uses, and further comprises the peptides themselves. A preferred method comprises the synthesis of simple periodic peptides made from polymerizing identical monomer units of four or fewer amino acids, wherein the minimum length of active peptide is 15 or 16 residues and wherein the minimum percentage of cationic residues is at least 25%.

116 Claims, No Drawings

```
                              SEQUENCE LISTING

<160> NUMBER OF SEQ ID NOS: 56

<210> SEQ ID NO 1
<211> LENGTH: 16
<212> TYPE: PRT
<213> ORGANISM: Unknown
<220> FEATURE:
<223> OTHER INFORMATION: Periodic Peptide

<400> SEQUENCE: 1

Lys Phe Ala Lys Lys Phe Ala Lys Lys Phe Ala Lys Lys Phe Ala Lys
1               5                   10                  15

<210> SEQ ID NO 2
<211> LENGTH: 20
<212> TYPE: PRT
<213> ORGANISM: Unknown
<220> FEATURE:
<223> OTHER INFORMATION: Periodic Peptide

<400> SEQUENCE: 2

Lys Phe Ala Lys Lys Phe Ala Lys Lys Phe Ala Lys Lys Phe Ala Lys
1               5                   10                  15

Lys Phe Ala Lys
            20

<210> SEQ ID NO 3
<211> LENGTH: 24
<212> TYPE: PRT
<213> ORGANISM: Unknown
<220> FEATURE:
<223> OTHER INFORMATION: Periodic Peptide

<400> SEQUENCE: 3

Lys Phe Ala Lys Lys Phe Ala Lys Lys Phe Ala Lys Lys Phe Ala Lys
1               5                   10                  15

Lys Phe Ala Lys Lys Phe Ala Lys
            20

<210> SEQ ID NO 4
<211> LENGTH: 28
<212> TYPE: PRT
<213> ORGANISM: Unknown
<220> FEATURE:
<223> OTHER INFORMATION: Periodic Peptide

<400> SEQUENCE: 4

Lys Phe Ala Lys Lys Phe Ala Lys Lys Phe Ala Lys Lys Phe Ala Lys
1               5                   10                  15

Lys Phe Ala Lys Lys Phe Ala Lys Lys Phe Ala Lys
```

```
                20              25

<210> SEQ ID NO 5
<211> LENGTH: 32
<212> TYPE: PRT
<213> ORGANISM: Unknown
<220> FEATURE:
<223> OTHER INFORMATION: Periodic Peptide

<400> SEQUENCE: 5

Lys Phe Ala Lys Lys Phe Ala Lys Lys Phe Ala Lys Lys Phe Ala Lys
1               5                   10                  15

Lys Phe Ala Lys Lys Phe Ala Lys Lys Phe Ala Lys Lys Phe Ala Lys
            20                  25                  30

<210> SEQ ID NO 6
<211> LENGTH: 48
<212> TYPE: PRT
<213> ORGANISM: Unknown
<220> FEATURE:
<223> OTHER INFORMATION: Periodic Peptide

<400> SEQUENCE: 6

Lys Phe Ala Lys Lys Phe Ala Lys Lys Phe Ala Lys Lys Phe Ala Lys
1               5                   10                  15

Lys Phe Ala Lys Lys Phe Ala Lys Lys Phe Ala Lys Lys Phe Ala Lys
            20                  25                  30

Lys Phe Ala Lys Lys Phe Ala Lys Lys Phe Ala Lys Lys Phe Ala Lys
        35                  40                  45

<210> SEQ ID NO 7
<211> LENGTH: 68
<212> TYPE: PRT
<213> ORGANISM: Unknown
<220> FEATURE:
<223> OTHER INFORMATION: Periodic Peptide

<400> SEQUENCE: 7

Lys Phe Ala Lys Lys Phe Ala Lys Lys Phe Ala Lys Lys Phe Ala Lys
1               5                   10                  15

Lys Phe Ala Lys Lys Phe Ala Lys Lys Phe Ala Lys Lys Phe Ala Lys
            20                  25                  30

Lys Phe Ala Lys Lys Phe Ala Lys Lys Phe Ala Lys Lys Phe Ala Lys
        35                  40                  45

Lys Phe Ala Lys Lys Phe Ala Lys Lys Phe Ala Lys Lys Phe Ala Lys
    50                  55                  60

Lys Phe Ala Lys
65

<210> SEQ ID NO 8
<211> LENGTH: 84
<212> TYPE: PRT
<213> ORGANISM: Unknown
<220> FEATURE:
<223> OTHER INFORMATION: Periodic Peptide

<400> SEQUENCE: 8

Lys Phe Ala Lys Lys Phe Ala Lys Lys Phe Ala Lys Lys Phe Ala Lys
1               5                   10                  15

Lys Phe Ala Lys Lys Phe Ala Lys Lys Phe Ala Lys Lys Phe Ala Lys
            20                  25                  30

Lys Phe Ala Lys Lys Phe Ala Lys Lys Phe Ala Lys Lys Phe Ala Lys
```

```
                35                  40                  45
Lys Phe Ala Lys Lys Phe Ala Lys Lys Phe Ala Lys Lys Phe Ala Lys
        50                  55                  60
Lys Phe Ala Lys Lys Phe Ala Lys Lys Phe Ala Lys Lys Phe Ala Lys
65                  70                  75                  80

Lys Phe Ala Lys

<210> SEQ ID NO 9
<211> LENGTH: 24
<212> TYPE: PRT
<213> ORGANISM: Unknown
<220> FEATURE:
<223> OTHER INFORMATION: Periodic Peptide

<400> SEQUENCE: 9

Arg Phe Ala Arg Arg Phe Ala Arg Arg Phe Ala Arg Arg Phe Ala Arg
1               5                   10                  15

Arg Phe Ala Arg Arg Phe Ala Arg
            20

<210> SEQ ID NO 10
<211> LENGTH: 28
<212> TYPE: PRT
<213> ORGANISM: Unknown
<220> FEATURE:
<223> OTHER INFORMATION: Periodic Peptide

<400> SEQUENCE: 10

Arg Phe Ala Arg Arg Phe Ala Arg Arg Phe Ala Arg Arg Phe Ala Arg
1               5                   10                  15

Arg Phe Ala Arg Arg Phe Ala Arg Arg Phe Ala Arg
            20                  25

<210> SEQ ID NO 11
<211> LENGTH: 32
<212> TYPE: PRT
<213> ORGANISM: Unknown
<220> FEATURE:
<223> OTHER INFORMATION: Periodic Peptide

<400> SEQUENCE: 11

Arg Phe Ala Arg Arg Phe Ala Arg Arg Phe Ala Arg Arg Phe Ala Arg
1               5                   10                  15

Arg Phe Ala Arg Arg Phe Ala Arg Arg Phe Ala Arg Arg Phe Ala Arg
            20                  25                  30

<210> SEQ ID NO 12
<211> LENGTH: 24
<212> TYPE: PRT
<213> ORGANISM: Unknown
<220> FEATURE:
<223> OTHER INFORMATION: Periodic Peptide

<400> SEQUENCE: 12

Phe Ala Lys Lys Phe Ala Lys Lys Phe Ala Lys Lys Phe Ala Lys Lys
1               5                   10                  15

Phe Ala Lys Lys Phe Ala Lys Lys
            20

<210> SEQ ID NO 13
<211> LENGTH: 24
<212> TYPE: PRT
<213> ORGANISM: Unknown
```

-continued

```
<220> FEATURE:
<223> OTHER INFORMATION: Periodic Peptide

<400> SEQUENCE: 13

Ala Lys Lys Phe Ala Lys Lys Phe Ala Lys Lys Phe Ala Lys Lys Phe
1               5                   10                  15

Ala Lys Lys Phe Ala Lys Lys Phe
            20

<210> SEQ ID NO 14
<211> LENGTH: 24
<212> TYPE: PRT
<213> ORGANISM: Unknown
<220> FEATURE:
<223> OTHER INFORMATION: Periodic Peptide

<400> SEQUENCE: 14

Lys Lys Phe Ala Lys Lys Phe Ala Lys Lys Phe Ala Lys Lys Phe Ala
1               5                   10                  15

Lys Lys Phe Ala Lys Lys Phe Ala
            20

<210> SEQ ID NO 15
<211> LENGTH: 20
<212> TYPE: PRT
<213> ORGANISM: Unknown
<220> FEATURE:
<223> OTHER INFORMATION: Periodic Peptide

<400> SEQUENCE: 15

Leu Lys Lys Leu Leu Lys Lys Leu Leu Lys Lys Leu Leu Lys Lys Leu
1               5                   10                  15

Leu Lys Lys Leu
            20

<210> SEQ ID NO 16
<211> LENGTH: 24
<212> TYPE: PRT
<213> ORGANISM: Unknown
<220> FEATURE:
<223> OTHER INFORMATION: Periodic Peptide

<400> SEQUENCE: 16

Leu Lys Lys Leu Leu Lys Lys Leu Leu Lys Lys Leu Leu Lys Lys Leu
1               5                   10                  15

Leu Lys Lys Leu Leu Lys Lys Leu
            20

<210> SEQ ID NO 17
<211> LENGTH: 28
<212> TYPE: PRT
<213> ORGANISM: Unknown
<220> FEATURE:
<223> OTHER INFORMATION: Periodic Peptide

<400> SEQUENCE: 17

Leu Lys Lys Leu Leu Lys Lys Leu Leu Lys Lys Leu Leu Lys Lys Leu
1               5                   10                  15

Leu Lys Lys Leu Leu Lys Lys Leu Leu Lys Lys Leu
            20                  25

<210> SEQ ID NO 18
<211> LENGTH: 32
<212> TYPE: PRT
```

<213> ORGANISM: Unknown
<220> FEATURE:
<223> OTHER INFORMATION: Periodic Peptide

<400> SEQUENCE: 18

Leu Lys Lys Leu Leu Lys Lys Leu Leu Lys Lys Leu Leu Lys Lys Leu
1               5                   10                  15
Leu Lys Lys Leu Leu Lys Lys Leu Leu Lys Lys Leu Leu Lys Lys Leu
            20                  25                  30

<210> SEQ ID NO 19
<211> LENGTH: 28
<212> TYPE: PRT
<213> ORGANISM: Unknown
<220> FEATURE:
<223> OTHER INFORMATION: Periodic Peptide

<400> SEQUENCE: 19

Lys Phe Ala Phe Lys Phe Ala Phe Lys Phe Ala Phe Lys Phe Ala Phe
1               5                   10                  15
Lys Phe Ala Phe Lys Phe Ala Phe Lys Phe Ala Phe
            20                  25

<210> SEQ ID NO 20
<211> LENGTH: 28
<212> TYPE: PRT
<213> ORGANISM: Unknown
<220> FEATURE:
<223> OTHER INFORMATION: Periodic Peptide

<400> SEQUENCE: 20

Lys Phe Phe Lys Lys Phe Phe Lys Lys Phe Phe Lys Lys Phe Phe Lys
1               5                   10                  15
Lys Phe Phe Lys Lys Phe Phe Lys Lys Phe Phe Lys
            20                  25

<210> SEQ ID NO 21
<211> LENGTH: 28
<212> TYPE: PRT
<213> ORGANISM: Unknown
<220> FEATURE:
<223> OTHER INFORMATION: Periodic Peptide

<400> SEQUENCE: 21

Lys Phe Ala Lys Lys Phe Ala Lys Lys Phe Ala Lys Lys Phe Ala Lys
1               5                   10                  15
Lys Phe Ala Lys Lys Phe Ala Lys Lys Phe Ala Lys
            20                  25

<210> SEQ ID NO 22
<211> LENGTH: 28
<212> TYPE: PRT
<213> ORGANISM: Unknown
<220> FEATURE:
<223> OTHER INFORMATION: Periodic Peptide

<400> SEQUENCE: 22

Lys Ala Ala Lys Lys Ala Ala Lys Lys Ala Ala Lys Lys Ala Ala Lys
1               5                   10                  15
Lys Ala Ala Lys Lys Ala Ala Lys Lys Ala Ala Lys
            20                  25

<210> SEQ ID NO 23
<211> LENGTH: 28

<212> TYPE: PRT
<213> ORGANISM: Unknown
<220> FEATURE:
<223> OTHER INFORMATION: Periodic Peptide

<400> SEQUENCE: 23

Lys Lys Ala Lys Lys Lys Ala Lys Lys Lys Ala Lys Lys Lys Ala Lys
1               5                   10                  15

Lys Lys Ala Lys Lys Lys Ala Lys Lys Lys Ala Lys
            20                  25

<210> SEQ ID NO 24
<211> LENGTH: 15
<212> TYPE: PRT
<213> ORGANISM: Unknown
<220> FEATURE:
<223> OTHER INFORMATION: Periodic Peptide

<400> SEQUENCE: 24

Lys Phe Lys Lys Phe Lys Lys Phe Lys Lys Phe Lys Lys Phe Lys
1               5                   10                  15

<210> SEQ ID NO 25
<211> LENGTH: 18
<212> TYPE: PRT
<213> ORGANISM: Unknown
<220> FEATURE:
<223> OTHER INFORMATION: Periodic Peptide

<400> SEQUENCE: 25

Lys Phe Lys Lys Phe Lys Lys Phe Lys Lys Phe Lys Lys Phe Lys Lys
1               5                   10                  15

Phe Lys

<210> SEQ ID NO 26
<211> LENGTH: 21
<212> TYPE: PRT
<213> ORGANISM: Unknown
<220> FEATURE:
<223> OTHER INFORMATION: Periodic Peptide

<400> SEQUENCE: 26

Lys Phe Lys Lys Phe Lys Lys Phe Lys Lys Phe Lys Lys Phe Lys Lys
1               5                   10                  15

Phe Lys Lys Phe Lys
            20

<210> SEQ ID NO 27
<211> LENGTH: 24
<212> TYPE: PRT
<213> ORGANISM: Unknown
<220> FEATURE:
<223> OTHER INFORMATION: Periodic Peptide

<400> SEQUENCE: 27

Lys Phe Lys Lys Phe Lys Lys Phe Lys Lys Phe Lys Lys Phe Lys Lys
1               5                   10                  15

Phe Lys Lys Phe Lys Lys Phe Lys
            20

<210> SEQ ID NO 28
<211> LENGTH: 27
<212> TYPE: PRT
<213> ORGANISM: Unknown
<220> FEATURE:

<223> OTHER INFORMATION: Periodic Peptide

<400> SEQUENCE: 28

Lys Phe Lys Lys Phe Lys Lys Phe Lys Lys Phe Lys Lys Phe Lys Lys
1               5                   10                  15

Phe Lys Lys Phe Lys Lys Phe Lys Lys Phe Lys
            20                  25

<210> SEQ ID NO 29
<211> LENGTH: 30
<212> TYPE: PRT
<213> ORGANISM: Unknown
<220> FEATURE:
<223> OTHER INFORMATION: Periodic Peptide

<400> SEQUENCE: 29

Lys Phe Lys Lys Phe Lys Lys Phe Lys Lys Phe Lys Lys Phe Lys Lys
1               5                   10                  15

Phe Lys Lys Phe Lys Lys Phe Lys Lys Phe Lys Lys Phe Lys
            20                  25                  30

<210> SEQ ID NO 30
<211> LENGTH: 36
<212> TYPE: PRT
<213> ORGANISM: Unknown
<220> FEATURE:
<223> OTHER INFORMATION: Periodic Peptide

<400> SEQUENCE: 30

Lys Phe Lys Lys Phe Lys Lys Phe Lys Lys Phe Lys Lys Phe Lys Lys
1               5                   10                  15

Phe Lys Lys Phe Lys Lys Phe Lys Lys Phe Lys Lys Phe Lys Lys Phe
            20                  25                  30

Lys Lys Phe Lys
        35

<210> SEQ ID NO 31
<211> LENGTH: 48
<212> TYPE: PRT
<213> ORGANISM: Unknown
<220> FEATURE:
<223> OTHER INFORMATION: Periodic Peptide

<400> SEQUENCE: 31

Lys Phe Lys Lys Phe Lys Lys Phe Lys Lys Phe Lys Lys Phe Lys Lys
1               5                   10                  15

Phe Lys Lys Phe Lys Lys Phe Lys Lys Phe Lys Lys Phe Lys Lys Phe
            20                  25                  30

Lys Lys Phe Lys Lys Phe Lys Lys Phe Lys Lys Phe Lys Lys Phe Lys
        35                  40                  45

<210> SEQ ID NO 32
<211> LENGTH: 63
<212> TYPE: PRT
<213> ORGANISM: Unknown
<220> FEATURE:
<223> OTHER INFORMATION: Periodic Peptide

<400> SEQUENCE: 32

Lys Phe Lys Lys Phe Lys Lys Phe Lys Lys Phe Lys Lys Phe Lys Lys
1               5                   10                  15

Phe Lys Lys Phe Lys Lys Phe Lys Lys Phe Lys Lys Phe Lys Lys Phe
            20                  25                  30

```
Lys Lys Phe Lys Lys Phe Lys Lys Phe Lys Lys Phe Lys Lys Phe Lys
        35                  40                  45
Lys Phe Lys Lys Phe Lys Lys Phe Lys Lys Phe Lys Lys Phe Lys
    50                  55                  60
```

<210> SEQ ID NO 33
<211> LENGTH: 6
<212> TYPE: PRT
<213> ORGANISM: Unknown
<220> FEATURE:
<223> OTHER INFORMATION: Periodic Peptide

<400> SEQUENCE: 33

```
Phe Lys Ala Phe Lys Ala
1               5
```

<210> SEQ ID NO 34
<211> LENGTH: 12
<212> TYPE: PRT
<213> ORGANISM: Unknown
<220> FEATURE:
<223> OTHER INFORMATION: Periodic Peptide

<400> SEQUENCE: 34

```
Phe Lys Ala Phe Lys Ala Phe Lys Ala Phe Lys Ala
1               5                   10
```

<210> SEQ ID NO 35
<211> LENGTH: 18
<212> TYPE: PRT
<213> ORGANISM: Unknown
<220> FEATURE:
<223> OTHER INFORMATION: Periodic Peptide

<400> SEQUENCE: 35

```
Phe Lys Ala Phe Lys Ala Phe Lys Ala Phe Lys Ala Phe Lys Ala Phe
1               5                   10                  15

Lys Ala
```

<210> SEQ ID NO 36
<211> LENGTH: 21
<212> TYPE: PRT
<213> ORGANISM: Unknown
<220> FEATURE:
<223> OTHER INFORMATION: Periodic Peptide

<400> SEQUENCE: 36

```
Phe Lys Ala Phe Lys Ala Phe Lys Ala Phe Lys Ala Phe Lys Ala Phe
1               5                   10                  15

Lys Ala Phe Lys Ala
            20
```

<210> SEQ ID NO 37
<211> LENGTH: 24
<212> TYPE: PRT
<213> ORGANISM: Unknown
<220> FEATURE:
<223> OTHER INFORMATION: Periodic Peptide

<400> SEQUENCE: 37

```
Phe Lys Ala Phe Lys Ala Phe Lys Ala Phe Lys Ala Phe Lys Ala Phe
1               5                   10                  15

Lys Ala Phe Lys Ala Phe Lys Ala
            20
```

<210> SEQ ID NO 38
<211> LENGTH: 27
<212> TYPE: PRT
<213> ORGANISM: Unknown
<220> FEATURE:
<223> OTHER INFORMATION: Periodic Peptide

<400> SEQUENCE: 38

Phe Lys Ala Phe Lys Ala Phe Lys Ala Phe Lys Ala Phe Lys Ala Phe
1               5                   10                  15

Lys Ala Phe Lys Ala Phe Lys Ala Phe Lys Ala
            20                  25

<210> SEQ ID NO 39
<211> LENGTH: 30
<212> TYPE: PRT
<213> ORGANISM: Unknown
<220> FEATURE:
<223> OTHER INFORMATION: Periodic Peptide

<400> SEQUENCE: 39

Phe Lys Ala Phe Lys Ala Phe Lys Ala Phe Lys Ala Phe Lys Ala Phe
1               5                   10                  15

Lys Ala Phe Lys Ala Phe Lys Ala Phe Lys Ala Phe Lys Ala
            20                  25                  30

<210> SEQ ID NO 40
<211> LENGTH: 51
<212> TYPE: PRT
<213> ORGANISM: Unknown
<220> FEATURE:
<223> OTHER INFORMATION: Periodic Peptide

<400> SEQUENCE: 40

Phe Lys Ala Phe Lys Ala Phe Lys Ala Phe Lys Ala Phe Lys Ala Phe
1               5                   10                  15

Lys Ala Phe Lys Ala Phe Lys Ala Phe Lys Ala Phe Lys Ala Phe Lys
            20                  25                  30

Ala Phe Lys Ala Phe Lys Ala Phe Lys Ala Phe Lys Ala Phe Lys Ala
        35                  40                  45

Phe Lys Ala
    50

<210> SEQ ID NO 41
<211> LENGTH: 63
<212> TYPE: PRT
<213> ORGANISM: Unknown
<220> FEATURE:
<223> OTHER INFORMATION: Periodic Peptide

<400> SEQUENCE: 41

Phe Lys Ala Phe Lys Ala Phe Lys Ala Phe Lys Ala Phe Lys Ala Phe
1               5                   10                  15

Lys Ala Phe Lys Ala Phe Lys Ala Phe Lys Ala Phe Lys Ala Phe Lys
            20                  25                  30

Ala Phe Lys Ala Phe Lys Ala Phe Lys Ala Phe Lys Ala Phe Lys Ala
        35                  40                  45

Phe Lys Ala Phe Lys Ala Phe Lys Ala Phe Lys Ala Phe Lys Ala
    50                  55                  60

<210> SEQ ID NO 42

```
<211> LENGTH: 4
<212> TYPE: PRT
<213> ORGANISM: Unknown
<220> FEATURE:
<223> OTHER INFORMATION: Periodic Peptide

<400> SEQUENCE: 42

Leu Lys Leu Lys
1

<210> SEQ ID NO 43
<211> LENGTH: 10
<212> TYPE: PRT
<213> ORGANISM: Unknown
<220> FEATURE:
<223> OTHER INFORMATION: Periodic Peptide

<400> SEQUENCE: 43

Leu Lys Leu Lys Leu Lys Leu Lys Leu Lys
1               5                   10

<210> SEQ ID NO 44
<211> LENGTH: 16
<212> TYPE: PRT
<213> ORGANISM: Unknown
<220> FEATURE:
<223> OTHER INFORMATION: Periodic Peptide

<400> SEQUENCE: 44

Leu Lys Leu Lys Leu Lys Leu Lys Leu Lys Leu Lys Leu Lys Leu Lys
1               5                   10                  15

<210> SEQ ID NO 45
<211> LENGTH: 18
<212> TYPE: PRT
<213> ORGANISM: Unknown
<220> FEATURE:
<223> OTHER INFORMATION: Periodic Peptide

<400> SEQUENCE: 45

Leu Lys Leu Lys Leu Lys Leu Lys Leu Lys Leu Lys Leu Lys Leu Lys
1               5                   10                  15

Leu Lys

<210> SEQ ID NO 46
<211> LENGTH: 20
<212> TYPE: PRT
<213> ORGANISM: Unknown
<220> FEATURE:
<223> OTHER INFORMATION: Periodic Peptide

<400> SEQUENCE: 46

Leu Lys Leu Lys Leu Lys Leu Lys Leu Lys Leu Lys Leu Lys Leu Lys
1               5                   10                  15

Leu Lys Leu Lys
            20

<210> SEQ ID NO 47
<211> LENGTH: 22
<212> TYPE: PRT
<213> ORGANISM: Unknown
<220> FEATURE:
<223> OTHER INFORMATION: Periodic Peptide

<400> SEQUENCE: 47

Leu Lys Leu Lys Leu Lys Leu Lys Leu Lys Leu Lys Leu Lys Leu Lys
```

```
                1               5              10              15

Leu Lys Leu Lys Leu Lys
        20

<210> SEQ ID NO 48
<211> LENGTH: 24
<212> TYPE: PRT
<213> ORGANISM: Unknown
<220> FEATURE:
<223> OTHER INFORMATION: Periodic Peptide

<400> SEQUENCE: 48

Leu Lys Leu Lys Leu Lys Leu Lys Leu Lys Leu Lys Leu Lys Leu Lys
1               5                  10                  15

Leu Lys Leu Lys Leu Lys Leu Lys
        20

<210> SEQ ID NO 49
<211> LENGTH: 36
<212> TYPE: PRT
<213> ORGANISM: Unknown
<220> FEATURE:
<223> OTHER INFORMATION: Periodic Peptide

<400> SEQUENCE: 49

Leu Lys Leu Lys Leu Lys Leu Lys Leu Lys Leu Lys Leu Lys Leu Lys
1               5                  10                  15

Leu Lys Leu Lys Leu Lys Leu Lys Leu Lys Leu Lys Leu Lys Leu Lys
            20                  25                  30

Leu Lys Leu Lys
        35

<210> SEQ ID NO 50
<211> LENGTH: 48
<212> TYPE: PRT
<213> ORGANISM: Unknown
<220> FEATURE:
<223> OTHER INFORMATION: Periodic Peptide

<400> SEQUENCE: 50

Leu Lys Leu Lys Leu Lys Leu Lys Leu Lys Leu Lys Leu Lys Leu Lys
1               5                  10                  15

Leu Lys Leu Lys Leu Lys Leu Lys Leu Lys Leu Lys Leu Lys Leu Lys
            20                  25                  30

Leu Lys Leu Lys Leu Lys Leu Lys Leu Lys Leu Lys Leu Lys Leu Lys
            35                  40                  45

<210> SEQ ID NO 51
<211> LENGTH: 14
<212> TYPE: PRT
<213> ORGANISM: Unknown
<220> FEATURE:
<223> OTHER INFORMATION: Periodic Peptide

<400> SEQUENCE: 51

Leu Arg Leu Arg Leu Arg Leu Arg Leu Arg Leu Arg Leu Arg
1               5                  10

<210> SEQ ID NO 52
<211> LENGTH: 18
<212> TYPE: PRT
<213> ORGANISM: Unknown
<220> FEATURE:
<223> OTHER INFORMATION: Periodic Peptide
```

```
<400> SEQUENCE: 52

Leu Arg Leu Arg Leu Arg Leu Arg Leu Arg Leu Arg Leu Arg Leu Arg
1               5                   10                  15

Leu Arg

<210> SEQ ID NO 53
<211> LENGTH: 22
<212> TYPE: PRT
<213> ORGANISM: Unknown
<220> FEATURE:
<223> OTHER INFORMATION: Periodic Peptide

<400> SEQUENCE: 53

Leu Arg Leu Arg Leu Arg Leu Arg Leu Arg Leu Arg Leu Arg Leu Arg
1               5                   10                  15

Leu Arg Leu Arg Leu Arg
            20

<210> SEQ ID NO 54
<211> LENGTH: 33
<212> TYPE: PRT
<213> ORGANISM: Unknown
<220> FEATURE:
<223> OTHER INFORMATION: Periodic Peptide

<400> SEQUENCE: 54

Lys Gly Lys Lys Gly Lys Lys Gly Lys Lys Gly Lys Lys Gly Lys Lys
1               5                   10                  15

Gly Lys Lys Gly Lys Lys Gly Lys Lys Gly Lys Lys Gly Lys Lys Gly
            20                  25                  30

Lys

<210> SEQ ID NO 55
<211> LENGTH: 45
<212> TYPE: PRT
<213> ORGANISM: Unknown
<220> FEATURE:
<223> OTHER INFORMATION: Periodic Peptide

<400> SEQUENCE: 55

Lys Gly Lys Lys Gly Lys Lys Gly Lys Lys Gly Lys Lys Gly Lys Lys
1               5                   10                  15

Gly Lys Lys Gly Lys Lys Gly Lys Lys Gly Lys Lys Gly Lys Lys Gly
            20                  25                  30

Lys Lys Gly Lys Lys Gly Lys Lys Gly Lys Lys Gly Lys
        35                  40                  45

<210> SEQ ID NO 56
<211> LENGTH: 21
<212> TYPE: PRT
<213> ORGANISM: Unknown
<220> FEATURE:
<223> OTHER INFORMATION: Periodic Peptide

<400> SEQUENCE: 56

Lys Thr Lys Lys Thr Lys Lys Thr Lys Lys Thr Lys Lys Thr Lys Lys
1               5                   10                  15

Thr Lys Lys Thr Lys
            20
```

PERIODIC ANTIMICROBIAL PEPTIDES

PRIOR RELATED APPLICATIONS

This application claims priority to U.S. Provisional Application 60/560,737, filed Feb. 24, 2003.

FEDERALLY SPONSORED RESEARCH STATEMENT

Not applicable.

FIELD OF THE INVENTION

The invention comprises a novel process for producing periodic peptides, as well as the peptides themselves and the use of those peptides in a variety of therapeutic applications, such as antimicrobial, antibacterial, antiviral, or anti-tumor agents and other therapeutics, disinfectives, preservatives, and the like.

BACKGROUND OF THE INVENTION

Antimicrobial peptides are common weapons in the natural defense arsenal of many types of organisms, including mammals, birds, reptiles, insects, plants and many microorganisms. Naturally occurring antimicrobial peptides are unique sequences that are about 10 to 50 amino acids in length. They tend to be rich in basic amino acids (lysine and arginine) and thus cationic. They are also often amphipathic in nature (i.e., one part of the molecule is hydrophilic while the other part is hydrophobic).

Although widely studied, the mode of action of antimicrobial peptides remains the subject of scientific debate. In many cases, the data suggests that the amphipathic peptides organize to form pores or channels in membranes (Durell (1992)). In other experiments, the antimicrobial peptides appear to disrupt a membrane by forming a "carpet-like" association with the membrane (Gazit (1995)). Either mechanism disrupts and kills cells by causing membrane depolarization and the loss of essential cellular components.

Microbial selectivity stems from the difference between mammalian and microbial cells as to the lipid composition of the membranes. The outer leaflet of mammalian cell membranes is almost entirely composed of electrically neutral, zwitterionic phospholipids, mainly phosphatidylcholine, sphingomyelin and cholesterol. By contrast, bacterial membranes consist of mainly negatively charged phospholipids, such as phosphatidylglycerol and cardiolipin. Thus, bacterial cells are susceptible to the cationic antimicrobial peptides, while mammalian cells are not. There is also some evidence to suggest that cancer cells may also differ in their membrane components from normal mammalian cells, making tumor cells susceptible to antimicrobial peptides.

Antimicrobial peptides can also be expected to have efficacy against viruses, such as HIV, herpes simplex and cytomegalovirus. However, the mechanism differs slightly. A virus is generally immune to membrane-bursting mechanisms because of the outer protein coat, but several antimicrobial peptides have shown antiviral activity by either blocking fusion of the virus with the host cell wall (thereby preventing transmission of the genetic material into the host cell) or by inhibiting replication of the virus once the host cell wall has been breached.

In light of the widespread appearance of pathogens that are drug resistant, there is interest in using antimicrobial peptides as an alternative to typical small molecule drugs if they could be economically produced. However, a practical limitation to large-scale uses of antimicrobial peptides is that they are expensive to produce in mass quantities. For example, peptide synthesis is very costly because the peptides are of unique sequence. Each amino acid must be added to a growing peptide chain, usually with less than perfect efficiency. Thus, as chain length increases, yields decrease.

The recombinant production of proteins provides some advantages over solid phase synthesis, including sequence fidelity, convenience, low cost, and the ability to produce longer proteins. However, recombinant techniques cannot be universally applied, and the recombinant production of antimicrobial peptides is particularly difficult due to their tendency to kill a variety of host cells. Even when synthesized as inactive fusion proteins, the precursor must still be cleaved to liberate the active peptide and further purification is usually required. These additional steps increase the cost and decrease the yield of the recombinant protein.

Demegen, Inc. of Pittsburg, Pa. owns several peptides which are being developed for medical use. One is D2A21 (FAKKFAKKFKLKEAKKFAKLFAFAF) (SEQ. ID. No. 65) being developed under the trade name DEMEGEL.™ This unique antimicrobial peptide is an amphipathic α-helix peptide that uses groups of 4 and 3 amino acids in order to keep the polar and non-polar faces aligned (3.6 residues/turn). It is synthesized by traditional methods, one amino acid at a time.

D2A21 has activity against a variety of cell types, including *T. vaginalis, C. trachomatis*, and *P. aeruginosa*. Preliminary results have also established anti-tumor activity in a rat prostate adenocarcinoma model, improving the survival rates from 25% to 75% and not causing any significant toxicities. Although uncertain of the basis for this activity, it is suggested that tumor cell membranes are substantially different from those of normal cells and therefore more susceptible to lysis by antimicrobial peptides (Arlotti (2001)). Finally, D2A21 has also been shown to have activity against the herpes simplex virus (HSV). When mixed with a modified lipid octyl-glycerol, D2A21 was better than five other peptides (including magainins and defensins) against HSV.

Although very promising, peptides like D2A21 must be made one amino acid at a time, for a cost of about US $50–500/g. As another example, nisin is an antimicrobial peptide used in processed dairy products, which sells for approximately $6000/pound of active peptide.

An alternative approach is to design peptides that have a several-amino acid repeat unit. The short sequence of amino acids could be synthesized less expensively than a long peptide and the repeat unit oligomerized to reach the full peptide length. Recent efforts using this approach include U.S. Pat. No. 5,789,542 and Javadpour (1996). These references teach that 7 residue (7mer) repeat units, polymerized into 14 and 21 residue peptides, can form the basis for antimicrobial peptides. By using the 7mer, a "simulated" α-helix is made, complete with an 3.5 amino acids per turn. However, the 7mer is still quite expensive to synthesize, thus limiting this approach.

Desirably, a process would exist that could inexpensively produce peptides having comparable antimicrobial activity to unique peptides. More desirably, the antimicrobial peptides produced by such a process would not require adherence to the classical α-helix structure, so that small repeat units of fewer than 7 residues could be used to construct the final peptide. By virtue of their simplicity, the peptides would be inexpensive to make, yet have significant antimicrobial activity.

SUMMARY OF THE INVENTION

The invention comprises a method of producing antimicrobial periodic peptides and further comprises the peptides themselves and a wide variety of their uses.

In a preferred embodiment, simple peptides are made from monomer units of four or fewer amino acids. Identical monomers units are joined end to end until a minimum size of about 15–16 amino acids is reached. By designing periodic peptides that use only tetramer (4mer), trimer (3mer) or dimer (2mer) monomers, the cost of production is reduced substantially as compared to traditional custom synthesis methods. Further, even if a given peptide were less active on a performance per dose basis, the significantly lower production cost still results in reduced cost per unit dosage.

The monomers may be produced synthetically or through microbial, viral or enzymatic expression. The smaller the monomer, the lower the cost of preparation. Dimeric monomers units may be commercially available at low cost and are particularly preferred. Identical monomers may be multimerized one by one to control the ultimate size or as a mixture and then selected for size. Alternatively, mixtures of different sizes can also be employed and this is a particularly preferred embodiment.

Each monomer should contain a positively charged amino acid, such as lysine, arginine, and the like. The monomers should also contain a hydrophobic amino acid, such as alanine, valine, and the like, and preferably, at least one of the hydrophobic amino acids has a bulky side chain such as phenylalanine. However, no clear trends were detectable when peptide activity was compared against hydropathy.

It is preferred that at least 25% of the peptide (by number, not weight) be positively charged amino acids, and preferably at least 30%. Antimicrobial activity has been detected in periodic peptides with as much as 75% cationic residues.

Preferably, the overall chain length of the resulting peptide should be at least 14 to 16 amino acids in length, but activity has been detected in peptides as small as 4 residues. An upper size limit on activity has not yet been found, but even if active, it is expected that very large multimers will be susceptible to stability or systemic transport problems. Thus, we have suggested a practical limit of about 50, 80 or 100 residues, and preliminary results indicate that even peptides as long as 80 residues are active. Most preferably, the overall chain length of the resulting peptide is from about 14–40 or 16–36 or 20–24 amino acids in length.

The peptides may contain either natural or synthetic amino acid with characteristics as described above. They may be made with either D or L amino acids. Peptides made with D amino acids have some advantage in being less susceptible to proteolytic degradation. Mixed peptides should be predominantly D (80%) in order to take advantage of this feature. Non-peptide linkages may also be employed in order to improve the stability of the "peptides." The peptides tested herein were not capped, but had free amino and carboxy termini. However, capping and derivatizing may be employed as needed.

"Antimicrobial activity" means activity against bacteria, yeast, fungi, and other protozoans at a level less than or equal to an IC50 of 125 ug/ml. Anti-bacterial and anti-fungal activities are similarly defined. "Biocidal activity" means having killing activity of less than or equal to 125 ppm for 3.5 log kill at 24 hr. "Antiviral activity" means activity against viruses at an IC50 of less than 5 mM, and preferably less than 1 mM. "Anti-tumor activity" means activity against a tumor cell at a level less than or equal to a TX50 of 250 µg/mL or (50% toxic dose).

Many periodic antimicrobial peptides can be made according to the general process. The general formulae for the monomers is P2N2, P3N, PN2, P2N, and NP, wherein P is any cationic residue and N is any hydrophobic residue and the N and P residues are in any order (in all cases the first and second P or N residues may be the same or differ within a given monomer). Preferred sequences include PNNP, NNPP, NPPN, PPNN, PNPN, NPNP, PNP, NPP, PPN, NPN, PNN, NNP, NP and PN. Preferably, the P can be any of K (lysine), O (omathine), or R (arginine) and N can be any of A (alanine), F (phenylalanine), G (glycine), L (leucine), I (isoleucine), T (threonine), Y (tyrosine), W (tryptophan), V (valine), or M (methionine).

The periodic peptides have a wide variety of applications, including agricultural (use in fields, orchards, vineyards, gardens, etc., for control of bacterial, fungal and viral pests); post harvest grain, fruit, and vegetable treatments; veterinary use; personal hygiene products; baby products; personal wipes; hard surface disinfectants; pharmaceutical uses to treat infections and tumors; skin treatments (dandruff, acne, psoriasis); drug permeability enhancers; medical device treatments; eye treatments (infection control, contact lens disinfection, contact lens solution preservative); pharmaceutical preservatives (such as vaccines); personal care product preservation; household product preservation; food, feed processing; meat processing disinfectant; potable water, juice and beverage preservative; and food & feed preservatives. They may also be the active ingredient in liquid soaps, toothpaste; hard surface cleaners and disinfectants; bathroom and kitchen cleaners; deodorants, textile and skin treatments, and the like.

EXAMPLE 1

Periodic peptides were ordered from a commercial peptide manufacturer for the initial antimicrobial tests. The antimicrobial peptides tested to date include those listed in Table 1. The ends of the peptides were not capped (free H and OH).

TABLE 1

Specific Periodic Peptide Sequences

| SEQ ID NO | SEQUENCE |
| --- | --- |
| 1. | KFAK KFAK KFAK KFAK |
| 2. | KFAK KFAK KFAK KFAK KFAK |
| 3. | KFAK KFAK KFAK KFAK KFAK KFAK |
| 4. | KFAK KFAK KFAK KFAK KFAK KFAK KFAK |
| 5. | KFAK KFAK KFAK KFAK KFAK KFAK KFAK KFAK |
| 6. | KFAK KFAK KFAK KFAK KFAK KFAK KFAK KFAK KFAK KFAK KFAK KFAK |
| 7. | KFAK KFAK KFAK KFAK KFAK KFAK KFAK KFAK KFAK KFAK KFAK KFAK KFAK KFAK KFAK KFAK |
| 8. | KFAK KFAK KFAK KFAK KFAK KFAK KFAK KFAK KFAK KFAK KFAK KFAK KFAK KFAK KFAK KFAK KFAK KFAK KFAK KFAK KFAK |

TABLE 1-continued

Specific Periodic Peptide Sequences

| SEQ ID NO | SEQUENCE |
|---|---|
| 9. | RFAR RFAR RFAR RFAR RFAR RFAR |
| 10. | RFAR RFAR RFAR RFAR RFAR RFAR RFAR |
| 11. | RFAR RFAR RFAR RFAR RFAR RFAR RFAR RFAR |
| 12. | FAKK FAKK FAKK FAKK FAKK FAKK |
| 13. | AKKF AKKF AKKF AKKF AKKF AKKF |
| 14. | KKFA KKFA KKFA KKFA KKFA KKFA |
| 15. | LKKL LKKL LKKL LKKL LKKL |
| 16. | LKKL LKKL LKKL LKKL LKKL LKKL |
| 17. | LKKL LKKL LKKL LKKL LKKL LKKL LKKL |
| 18. | LKKL LKKL LKKL LKKL LKKL LKKL LKKL LKKL |
| 19. | KFAF KFAF KFAF KFAF KFAF KFAF KFAF |
| 20. | KFFK KFFK KFFK KFFK KFFK KFFK KFFK |
| 21. | KFAK KFAK KFAK KFAK KFAK KFAK KFAK |
| 22. | KAAK KAAK KAAK KAAK KAAK KAAK KAAK |
| 23. | KKAK KKAK KKAK KKAK KKAK KKAK KKAK |
| 24. | KFK KFK KFK KFK KFK |
| 25. | KFK KFK KFK KFK KFK KFK |
| 26. | KFK KFK KFK KFK KFK KFK KFK |
| 27. | KEK KFK KFK KFK KFK KFK KFK KFK |
| 28. | KFK KFK KFK KFK KFK KFK KFK KFK KFK |
| 29. | KFK KFK KFK KFK KFK KFK KEK KFK KFK KFK |
| 30. | KFK KFK KFK KFK KFK KFK KFK KFK KFK KFK KFK KFK |
| 31. | KFK KFK KFK KFK KFK KFK KFK KFK KFK KFK KFK KFK KFK KFK KFK KFK |
| 32. | KFK KFK KFK KFK KFK KFK KFK KFK KFK KFK KFK KFK KFK KFK KFK KFK KFK KFK KFK KFK KFK |
| 33. | FKA FKA |
| 34. | FKA FKA FKA FKA |
| 35. | FKA FKA FKA FKA FKA |
| 36. | FKA FKA FKA FKA FKA FKA FKA |
| 37. | FKA FKA FKA FKA FKA FKA FKA FKA |
| 38. | FKA FKA FKA FKA FKA FKA FKA FKA FKA |
| 39. | FKA FKA FKA FKA FKA FKA FKA FKA FKA FKA |
| 40. | FKA FKA FKA FKA FKA FKA FKA FKA FKA FKA FKA FKA FKA FKA FKA |
| 41. | FKA FKA FKA FKA FKA FKA FKA FKA FKA FKA FKA FKA FKA FKA FKA FKA FKA |
| 42. | LK LK |
| 43. | LK LK LK LK LK |
| 44. | LK LK LK LK LK LK LK LK |
| 45. | LK LK LK LK LK LK LK LK LK |
| 46. | LK LK LK LK LK LK LK LK LK LK |
| 47. | LK LK LK LK LK LK LK LK LK LK LK |
| 48. | LK LK LK LK LK LK LK LK LK LK LK LK |
| 49. | LK LK LK LK LK LK LK LK LK LK LK LK LK LK LK LK LK |
| 50. | LK LK LK LK LK LK LK LK LK LK LK LK LK LK LK LK LK LK LK LK LK LK LK |
| 51. | LR LR LR LR LR LR LR |
| 52. | LR LR LR LR LR LR LR LR LR |
| 53. | LR LR LR LR LR LR LR LR LR LR LR |
| 54. | KGK KGK KGK KGK KGK KGK KGK KGK KGK KGK KGK |
| 55. | KGK KGK KGK KGK KGK KGK KGK KGK KGK KGK KGK KGK KGK KGK |
| 56. | KTK KTK KTK KTK KTK KTK KTK |

EXAMPLE 2

Antibacterial Testing

The MIC and IC50 values were determined by a broth microdilution method according to guidelines of the National Committee for Clinical Laboratory Standard as follows: In 96-well tissue culture plates, a fixed volume of bacterial suspension in 2× broth (as defined below) was added to the mixtures or individual compounds dispensed at concentrations varying from 1,000 to 1 μg/ml derived from serial two-fold dilutions in sterile water. The bacteria tested were *P. aeruginosa* American Type Culture Collection Number (ATCC) 10145, *E. coli* ATCC 2592, and *S. aureus* (methicillin reseistant) ATTC 33591.

All experiments were compared to bacterial growth under optimal growth conditions (37° C., pH 7.0, absence of additional salt, growth media—referred to as standard growth conditions). In each plate, no growth control (media alone), positive growth control (bacteria with no test sample), positive antimicrobial controls (agents with known antimicrobial activity) and test compounds were tested. Positive controls included non-periodic antimicrobial peptides D2A21 (FAKKFAKKFKKFAKKFAKFAFAF) (Seq. ID. No. 65) and D4E1 (FKLRAKIKVRLRAKIKL) (SEQ. ID. No. 66).

The plates were incubated overnight, and the relative percent growth determined by optical density at 620 nm (OD620) using a TITERTEK MULTISKAN PLUS™. MIC was defined as the lowest concentration of test sample resulting in 98% growth inhibition. IC50 values were calculated using a sigmoidal curve fitting software program (GRAPHPAD,™ ISI Software,™ San Diego, Calif.). All samples were tested in duplicate and each assay was repeated at least twice. In the following table, KFAK is the repeat unit and multimers of KFAK were tested. IC50 and MIC are reported in µg/ml.

TABLE 2

(KFAK)n Anti-microbial Activity Against *P. aeruginosa*:

| N | SEQ ID NO | IC50 | MIC |
|---|---|---|---|
| D2A21 | 65 | 11.3 | 32–64 |
| 1 | 57 | >250 | >250 |
| 2 | 58 | >250 | >250 |
| 3 | 59 | >250 | >250 |
| 4 | 1 | 116 | >250 |
| 5 | 2 | 7.7 | 16–32 |
| 6 | 3 | 5.6 | 16–32 |
| 7 | 4 | 12 | 16–32 |

Unexpectedly, these periodic peptides performed as well or better than their unique counterpart (D2A21). Encouraged by this surprising result, a wide variety of periodic peptides were made and tested for anti-bacterial activity using the same protocols. The results are shown below.

TABLE 3

Periodic Peptides and Anti-Bacterial Activity

| Number of Amino Acids | | SEQ ID NO | *P aeruginosa*, 10145 gram− | | *E. coli* 2592 gram− | | *S. aureus* (methicillin resistant), 33591 gram+ | |
|---|---|---|---|---|---|---|---|---|
| | | | IC50 (µg/ml) | MIC (µg/ml) | IC50 (µg/ml) | MIC (µg/ml) | IC50 (µg/ml) | MIC (µg/ml) |
| | D2A21 | 65 | 11.3 | 32–62 | 4.5 | 8–16 | 11.9 | 62–125 |
| | D4E1 | 66 | 6.2 | 8–16 | 3.3 | 8–16 | 6.3 | 32–62 |
| 4 | KFAK (1) | 57 | >500 | 500 | >250 | >250 | >500 | >500 |
| 8 | KFAK (2) | 58 | >250 | 250 | >250 | >250 | >250 | >250 |
| 12 | KFAK (3) | 59 | >500 | 500 | >250 | >250 | >500 | >500 |
| 16 | KFAK (4) | 1 | 85 | 125 | 46 | 62–125 | >250 | >250 |
| 20 | KFAK (5) | 2 | 5.5 | 8 | 6 | 16–32 | >250 | >250 |
| 24 | KFAK (6) | 3 | 5.6 | 16 | 4 | 8–16 | 38.7 | 125–250 |
| 28 | KFAK (7) | 4 | 12.2 | 16 | 8 | 32–62 | 108.8 | >250 |
| 32 | KFAK (8) | 5 | 19 | 20 | 12 | 16–32 | 40 | 125–250 |
| 24 | RFAR (6) | 9 | 25 | 32 | 12 | 31–62 | 15 | 31–62 |
| 28 | RFAR (7) | 10 | 20 | 62 | 8 | 32–62 | 31 | 125–250 |
| 32 | RFAR (8) | 11 | 30 | 62 | 12 | 32–62 | 20 | 125–250 |
| 24 | FAKK (6) | 12 | 21 | 62 | 11 | 17–32 | 108 | >250 |
| 24 | AKKF (6) | 13 | 21 | 25 | 8 | 16–32 | 41 | 125–250 |
| 24 | KKFA (6) | 14 | 33 | 62 | 7 | 16–32 | 136 | >250 |
| 20 | LKKL (5) | 15 | 27 | 62 | 49 | 62–125 | 69 | >250 |
| 24 | LKKL (6) | 16 | 58 | 65 | 31 | 62–125 | 98 | >250 |
| 28 | LKKL (7) | 17 | 96 | 125 | 41 | 62–125 | 252 | >250 |
| 32 | LKKL (8) | 18 | 61 | 125 | 37 | 62–125 | 80 | >250 |
| 28 | KFAF (7) | 19 | 250 | >250 | >1000 | >1000 | >500 | >500 |
| 28 | KFFK (7) | 20 | 87 | 125 | 63 | >125 | 133 | >250 |
| 28 | KFAK (7) | 21 | 12.2 | 16 | 8 | 32–62 | 108.8 | >250 |
| 28 | KAAK (7) | 22 | >250 | >250 | 261 | 500- | >500 | >500 |
| 28 | KKAK (7) | 23 | 99 | 125 | 26 | 31–62 | 60 | 0 |
| 18 | KFK (6) | 25 | 74 | 125 | 39 | 62–125 | 322 | >500 |
| 21 | KFK (7) | 26 | 87 | 125 | 18 | 31–62 | 141 | >500 |
| 24 | KFK (8) | 27 | 145 | 250 | 20 | 32–62 | 72 | >250 |
| 27 | KFK (9) | 28 | 68 | 125 | 14 | 16–32 | 92 | 125–250 |
| 20 | KFK (10) | 29 | 31 | 62 | 10 | 12–16 | 59 | >250 |
| 18 | FKA (6) | 35 | 79 | 100 | 29 | 32–62 | >500 | >500 |
| 21 | FKA (7) | 36 | 23 | 32 | 7 | 16–32 | >500 | >500 |
| 24 | FKA (8) | 37 | 19 | 25 | 7 | 16–32 | 74 | >500 |
| 27 | FKA (9) | 38 | 16 | 20 | 4 | 31–62 | 17 | 31–62 |
| 30 | FKA (10) | 39 | 27 | 32 | 9 | 31–62 | 12 | 31–62 |
| 14 | LK (7) | 60 | 111 | 125 | 37 | 45–62 | 78 | 250–500 |
| 16 | LK (8) | 44 | 125 | 130 | 65 | >125 | 56 | 125–250 |
| 18 | LK (9) | 45 | 74 | 80 | 35 | 62–125 | 50 | 250–500 |
| 20 | LK (10) | 46 | 47 | 125 | 127 | 150–250 | 29 | 125–250 |
| 22 | LK (11) | 47 | 51 | 62 | 50 | >125 | 111 | >250 |
| 24 | LK (12) | 48 | 41 | 45 | 23 | 62–125 | 85 | >250 |
| 14 | LR (7) | 51 | 109 | 125 | 15 | 31–62 | 90 | 250–500 |

TABLE 3-continued

Periodic Peptides and Anti-Bacterial Activity

| Number of Amino Acids | SEQ ID | ID NO | P aeruginosa, 10145 gram– | | E. coli 2592 gram– | | S. aureus (methicillin resistant), 33591 gram+ | |
|---|---|---|---|---|---|---|---|---|
| | | | IC50 (μg/ml) | MIC (μg/ml) | IC50 (μg/ml) | MIC (μg/ml) | IC50 (μg/ml) | MIC (μg/ml) |
| 18 | LR (9) | 52 | >250 | >250 | 70 | >125 | 28 | 125–250 |
| 22 | LA (11) | 53 | >250 | >250 | 96 | 125–250 | 39 | 125–250 |
| *PBF16a | | 67 | >250 | >250 | / | / | / | / |
| **PBF16b | | 68 | >250 | >250 | / | / | / | / |
| ***PBF16c | | 69 | >250 | >250 | / | / | / | / |

*PBF16a = KFAKKFAKKFAKKAAK (non-periodic)
**PBF16b = KFAKKFAKKAAKKAAK (non-periodic)
***PBF16c = KFAKKAAKKFAKKAAK (non-periodic)

In reviewing these results, several patterns readily emerge. First, it is clear that periodic peptides made of monomer units as small as a 2mer may be shown to exhibit strong antimicrobial activity (e.g., LK(7–12)). This is very surprising given that most antimicrobial peptides teach that the helix structure must be maintained and employs repeated 7mers to that end and there are very few antimicrobial peptides with beta pleated sheet structures.

Second, its appears that larger peptides have more efficacy than smaller ones. For example, peptides should be at least as big as about 14–16 amino acids to display optimal efficacy (compare KFAK(1–3) versus KFAK(4–8)).

Third, the periodic peptides in many instance demonstrate better activity than the prior art unique peptides (compare D2A21 and D4E1 versus FKAK(5)). This is particularly useful because it means that periodic peptides with equal or better efficacy can be used instead of the prior art unique peptides resulting in substantial cost savings.

Fourth, the tested non-periodic peptides having similar residue content do not display antimicrobial activity (see PBF16a–c).

EXAMPLE 3

Anti-Fungal Testing

Because the antibacterial activity of the periodic peptides was so promising, further experiments were performed to determine if the periodic peptides also had antifungal activity. The experimental design was similar to that above, with accommodation made for fungal growth requirements, including the use of Sabouraud Dextrose Broth (SDB) and Sabouraud Dextrose Agar (SDA) slants.

TABLE 4

Periodic Peptides and Anti-Fungal Activity

| Number of Amino Acids | SEQ ID | ID NO | yeast - C. albicans - 10231 | | fungus - Cr. Neoformans - 32045 | |
|---|---|---|---|---|---|---|
| | | | IC50 (μg/ml) | MIC (μg/ml) | IC50 (μg/ml) | MIC (μg/ml) |
| | D2A21 | 65 | 121.5 | >250 | 21.9 | 62–125 |
| | D4E1 | 66 | 70.6 | 80–125 | 1.8 | 8–16 |
| 4 | KFAK (1) | 57 | 329 | >500 | 400 | >500 |

TABLE 4-continued

Periodic Peptides and Anti-Fungal Activity

| Number of Amino Acids | SEQ ID | ID NO | yeast - C. albicans - 10231 | | fungus - Cr. Neoformans - 32045 | |
|---|---|---|---|---|---|---|
| | | | IC50 (μg/ml) | MIC (μg/ml) | IC50 (μg/ml) | MIC (μg/ml) |
| 8 | KFAK (2) | 58 | >250 | >250 | >250 | >250 |
| 12 | KFAK (3) | 59 | 262 | 280–500 | 22 | 125–250 |
| 16 | KFAK (4) | 1 | 70 | 90–125 | 5.3 | 6.0–8.0 |
| 20 | KFAK (5) | 2 | 66 | 90–125 | 5 | 8–16 |
| 24 | KFAK (6) | 3 | 72 | 80–125 | 5.8 | 16–32 |
| 28 | KFAK (7) | 4 | 82 | 100–125 | 9.1 | 32–62 |
| 32 | KFAK (8) | 5 | 105 | 125–250 | 4.1 | 8–16 |
| 24 | RFAR (6) | 9 | 114 | 125–250 | 35 | 62–125 |
| 28 | RFAR (7) | 10 | 172 | 250–500 | 45 | 62–125 |
| 32 | RFAR (8) | 11 | 144 | 250–500 | 32 | 62–125 |
| 24 | FAKK (6) | 12 | 110 | 125–250 | 7.6 | 16–32 |
| 24 | AKKF (6) | 13 | 225 | 250–500 | 11 | 16–32 |
| 24 | KKFA (6) | 14 | 107 | 125–250 | 12 | 32–62 |
| 20 | LKKL (5) | 15 | 211 | >500 | 55 | 62–125 |
| 24 | LKKL (6) | 16 | 213 | 250–500 | 93 | >125 |
| 28 | LKKL (7) | 17 | 199 | 250–500 | 85 | 100–125 |
| 32 | LKKL (8) | 18 | 179 | 250–500 | 56 | 62–125 |
| 28 | KFAF (7) | 19 | >500 | >500 | 67 | 125–250 |
| 28 | KFFK (7) | 20 | 183 | 250–500 | 55 | 62–125 |
| 28 | KFAK (7) | 21 | 82 | 100–125 | 9 | 32–62 |
| 28 | KAAK (7) | 22 | 262 | >500 | 41 | 62–125 |
| 28 | KKAK (7) | 23 | >500 | >500 | 28 | >63 |
| 18 | KFK (6) | 25 | 164 | 250–500 | 33 | 40–62 |
| 21 | KFK (7) | 26 | 175 | 250–500 | 26 | 40–62 |
| 24 | KFK (8) | 27 | 113 | 125–250 | 25 | 40–62 |
| 27 | KFK (9) | 28 | 194 | 250–500 | 39 | 62–125 |
| 20 | KFK (10) | 29 | 104 | 125–250 | 30 | 40–62 |
| 18 | FKA (6) | 35 | 208 | 250–500 | 2.8 | 4–8 |
| 21 | FKA (7) | 36 | 203 | 250–500 | 3.2 | 4–8 |
| 24 | FKA (8) | 37 | 199 | 250–500 | 3.9 | 16–32 |
| 27 | FKA (9) | 38 | 195 | 250–500 | 16 | 62–125 |
| 30 | FKA (10) | 39 | 182 | 250–500 | 20 | 32–62 |
| 14 | LK (7) | 60 | 166 | 250–500 | 0.8 | 2–4 |
| 16 | LK (8) | 44 | 162 | 250–500 | 9.7 | 32–63 |
| 18 | LK (9) | 45 | 216 | 250–500 | 4.9 | 32–62 |
| 20 | LK (10) | 46 | 187 | 250–500 | 3.0 | 62–125 |
| 22 | LK (11) | 47 | 185 | 250–500 | 26 | 32–62 |
| 24 | LK (12) | 48 | 175 | 250–500 | 22 | 32–62 |
| 14 | LR (7) | 51 | 182 | 250–500 | 1.8 | 4–8 |
| 18 | LR (9) | 52 | 195 | 250–500 | 21 | 62–125 |
| 22 | LR (11) | 53 | >500 | >500 | 3.3 | 62–125 |

The results show that some of the periodic peptides have highly effective against fungal pathogens (e.g., KFAF(7), KFK(10)), although most are species specific.

EXAMPLE 4

Anti-Tumor Testing

Encouraged by the strong antimicrobial activity of the periodic peptides, tumor cells were also tested. Red blood cells (RBC) were used to ascertain that the periodic peptides would not kill normal mammalian cells, which would obviously limit their effectiveness.

The RBC protocol was from Blondelle (2000) and is described generally as follows: The toxicity toward the HeLa cell line was determined using a MTS (3-(4-5-dimethylthiazol-2-yl)-5-(3carboxymethoxyphenyl)-2-(4-sulfophenyl)-2H-tetrazolium, sodium salt) cellular reduction assay. MTS (2 mg/mL) was prepared in Dulbecco PBS (pH 7.35), filtered, aliquoted and stored at minus 20° C. In 96 well flat bottomed plates, cell suspensions (250 µL of 6×10$^4$ cell/mL in each well) were incubated for 48 h at 37° C. (5% CO2 incubator). The peptides (50 µL) were then added to the cell monolayer (following aspiration of the media from each well and addition of 50 µL of Dulbecco's Modified Eagles Medium) at varying concentrations derived from serial 2-fold dilutions, and the plates incubated for 24 h at 37° C. (5% CO2 incubator). Proliferation was then determined by adding a solution of phenazine methosulfate (PMS: 0.92 mg/mL in DPBS) to MTS at a 1:20 ration just prior to the assay. Twenty microliters MTS-PMS solution were added to each well and the plates incubated for 1 h at 37° C. (5% CO2 incubator). The relative percent toxicity was determined by comparing the absorbance at 490 nm of each peptide to the absorbance of cells without peptide. The TX50 (concentration required for 50% toxicity) was calculated using a sigmoidal curve fitting software (Graphpad Prism).

TABLE 5

Periodic Peptides and Anti-Tumor Activity

| Number of Amino Acids | ID | SEQ ID NO | RBCs TX50 (µg/ml) | RBCs % kill at 250 µg/ml | HeLa TX50 (µg/ml) | HeLa % kill at 500 µg/ml |
|---|---|---|---|---|---|---|
|  | D2A21 | 64 | 52 | 93.1 | 16.9 | 7.1 |
|  | D4E1 | 65 | 133.6 | 77.2 | >500 | 55.2 |
| 4 | KFAK (1) | 57 | >500 | 2.8% | >500 | 112 |
| 8 | KFAF (2) | 58 | >250 | 2.2% | >500 | 83 |
| 12 | KFAK (3) | 59 | >500 | 0.4% | >500 | 77 |
| 16 | KFAK (4) | 1 | >250 | 0.1% | >500 | 76 |
| 20 | KFAK (5) | 2 | >250 | 4.1% | >500 | 89 |
| 24 | KFAK (6) | 3 | >250 | 7.3 | 457.3 | 30.5 |
| 28 | KFAK (7) | 4 | >250 | 13.7 | 204.1 | 13.0 |
| 32 | KFAK (8) | 5 | >500 | 48% | 249 | 18.2% |
| 24 | RFAR (6) | 9 | 176 | 72% | 159 | 22.1% |
| 28 | RFAR (7) | 10 | 20 | 100% | 106 | 12.4% |
| 32 | RFAR (8) | 11 | 17 | 100% | 71 | 9.5% |
| 24 | FAKK (6) | 12 | >500 | 7% | 359 | 28.3% |
| 24 | AKKF (6) | 13 | 39 | 100% | 33 | 7.3% |
| 24 | KKFA (6) | 14 | >500 | 2% | >500 | 76.4% |
| 20 | LKKL (5) | 15 | 9 | 100% | 31 | −0.7% |
| 24 | LKKL (6) | 16 | 11 | 100% | 26 | −1.3% |
| 28 | LKKL (7) | 17 | 9 | 100% | 25 | −0.4% |
| 32 | LKKL (8) | 18 | 8 | 100% | 23 | 0.1% |
| 28 | KFAF (7) | 19 | >500 | 4% | >500 | 76.8% |
| 28 | KFFK (7) | 20 | 12 | 100% | 30 | −0.5% |
| 28 | KFAK (7) | 21 | >250 | 13.7 | 204.1 | 13.0 |
| 28 | KAAK (7) | 22 | >500 | −6% | >500 | 90.0% |
| 28 | KKAK (7) | 23 | >500 | −6% | >500 | >87.9% |
| 18 | KFK (6) | 25 | >500 | −7% | >500 | 77.8% |
| 21 | KFK (7) | 26 | >500 | −7% | >500 | 80.9% |
| 24 | KFK (8) | 27 | >500 | −6% | >500 | 84.2% |
| 27 | KFK (9) | 28 | >500 | −6% | >500 | 80.7% |
| 20 | KFK (10) | 29 | >500 | 3% | >500 | 56.8% |
| 18 | FKA (6) | 35 | 496 | 28% | >500 | 110.8% |
| 21 | FKA (7) | 36 | >500 | 11% | >500 | 103.3% |
| 24 | FKA (8) | 37 | >500 | 10% | >500 | 60.4% |
| 27 | FKA (9) | 38 | >500 | 24% | 389 | 20.9% |
| 30 | FKA (10) | 39 | >500 | 51% | 234 | 15.0% |
| 14 | LK (7) | 60 | >500 | 16% | 309 | 29.6% |
| 16 | LK (8) | 44 | >500 | 13% | 122 | 43.5% |
| 18 | LK (9) | 45 | >500 | 21% | 137 | 46.0% |
| 20 | LK (10) | 46 | >500 | 27% | >500 | 65.0% |
| 22 | LK (11) | 47 | >500 | 24% | 202 | 43.8% |
| 24 | LK (12) | 48 | >500 | 35% | 49 | 60.0% |
| 14 | LR (7) | 51 | >500 | 15% | >500 | 86.5% |
| 18 | LR (9) | 52 | >500 | 24% | >500 | 96.7% |
| 22 | LR (11) | 53 | 450 | 41% | >500 | 66.6% |

As expected, some of the periodic peptides have anti-tumor activity, but do not destroy normal cells such as red blood cells (RBCs). In particular, the dipeptides LK(8–9, 12) appear very promising; killing HeLa cells, but not RBCs. However, anti-tumor activity is less predictable than antimicrobial activity, and each periodic peptide should be tested against a range of cells before use.

EXAMPLE 5

Biocidal Testing

In the previous experiment, IC50 and MIC were measured because these are simple, common tests that are easy to perform. However, these tests actually measure biostat activity, and not true biocidal activity. Thus, biocidal activity was measured in this example.

Biocide efficacy protocols were improved by reducing sample size, organizing the test material into an array format, implementing most probable number (MPN) quantitation and using multi-channel liquid handling equipment. We call the new method "high-throughput microanalysis and rapid quantitation" or "HMARQ." HMARQ is directly applicable to current industrial efficacy tests such as multi-cycle preservation challenge or time course disinfection tests.

HMARQ is performed in a high throughput plate, such as 96-well microtiter plates. Typical sample volumes have been reduced down to 200 to 300 µL, but can be reduced further if desired. In these samples, no more than 10% of the total volume will be composed of the biocide and organism solution, and all non-matrix additions are normalized for all samples.

The sample matrix is first inoculated with the desired concentration of microorganisms. Inoculated sample matrix is then added to the 96-well assay block containing the biocide(s) under study. Each sample block contains biocide treated samples and untreated control samples (lacking biocide). Once the samples are prepared, the entire block of samples is mixed by vortexing until each sample is homogenous. In general, the study starts once mixing is complete, and samples are removed as required for the analysis. When Kill Time testing (rate of biocide activity) is performed, the microorganisms are added after biocide addition to the samples, allowing for rapid mixing and analysis.

Bacterial concentration (CFU/mL) is determined using the most probable number method (MPN). The contaminated solution is serially diluted until the "no growth" endpoint is reached. The endpoint represents the MPN and is expressed in units of the bacterial concentration. A serial 1:10 dilution will yield a bacterial concentration resolution of 1 log and the log reduction is determined by comparing the concentration of organisms in a treated sample to the concentration of organisms in untreated samples. For example, if a sample requires four 1:10 dilutions before bacterial growth is lost then the MPN for bacterial concentration in the sample is less than or equal to $1 \times 10^4$ CFU/mL (1E4). If each well in a serial 8-fold dilution shows bacterial growth, then the MPN is greater than or equal to $1 \times 10^8$ CFU/mL (1E8). This method of enumeration is generally applicable to all non-filamentous microorganisms.

Media included Tryptic Soy Broth (TSB) for bacteria and Sabouraud Dextrose Broth (SDB) for fungi. These are available commercially and prepared according to the manufacturers instructions. Indicator medium was TSB/R for bacteria and SDB/R for fungi. These were made by addition of 50 µM filter sterilized Resazurin to the sterilized and cooled medium. Tryptic Soy agar plates (TSA) and SDA slants were used to provide inoculant for bacterial and fungal cultures. The indicator dye appeared pink or white when bacterial growth was present. Blue indicated no growth and purple indicated that growth was present and would resolve with additional time.

Using the HMARQ test described above, periodic peptides were generated and tested for Kill Activity. In this experiment, a broader range of peptidezs were tested for activity. Units are expressed as ppm (µg/mL) needed for 3.5 log kill at 15 min or 24 hour and the results are shown below.

TABLE 6

Periodic Peptides and Biocidal Activity

| Number of Amino Acids | ID | SEQ ID NO | P. aeruginosa ATCC 15442 (gram−) | | Staph. aureus ATCC 6538 (gram+) | |
|---|---|---|---|---|---|---|
| | | | 15 min | 24 hr | 15 min | 24 hr |
| 32 | KFAK(8) | 5 | 31 | 31 | >500 | 8 |
| 36 | KFAK(12) | 6 | 16 | 31 | 31(3 log) | >500 |
| 52 | KFAK(17) | 7 | 16 | 250 | 250 | 500 |
| 80 | KFAK(20) | 61 | 8 | 16 | 4 | 4 |
| 28 | KKAK(7) | 23 | 16 | 16 | >500 | 125 |
| 28 | KFAF(7) | 19 | 63 | 63 | >500 | 125 |
| 24 | RFAR(6) | 9 | 31 | 31 | >500 | 8 |
| 28 | RFAR(7) | 10 | 63 | 125 | >500 | 4 |
| 32 | RFAR(8) | 11 | >500 | 16 | >500 | 125 |
| 24 | FAKK(6) | 12 | >500 | 16 | >500 | 250 |
| 24 | AKKF(6) | 13 | >500 | 16 | >500 | 125 |
| 24 | KKFA(6) | 14 | >500 | 8 | >500 | 63 |
| 20 | LKKL(5) | 15 | >500 | 8 | >500 | 125 |
| 24 | LKKL(6) | 16 | >500 | 8 | 4 | 125 |
| 28 | LKKL(7) | 17 | 125 | 8 | 4 | 125 |
| 32 | LKKL(8) | 18 | 4 | 8 | >500 | 125 |
| 28 | KFFK(7) | 20 | 16 | 8 | 4 | 63 |
| 28 | KAAK(7) | 22 | >500 | 125 | >500 | 250 |
| 9 | KFK(3) | 62 | >500 | 125 | >500 | >500 |
| 12 | KFK(4) | 63 | 500 | 125 | >500 | >500 |
| 18 | KFK(6) | 25 | >500 | 125 | >500 | |
| 21 | KFK(7) | 26 | >500 | 125 | >500 | |
| 24 | KFK(8) | 27 | >500 | >125 | >500 | 500 |
| 27 | KFK(9) | 28 | >500 | 63 | >500 | 500 |
| 30 | KFK(10) | 29 | 8 | 8 | 4 | 500 |
| 36 | KFK(12) | 30 | 4 | 8 | >500 | 250 |
| 48 | KFK(16) | 31 | 16 | 31 | >500 | 16 |
| 63 | KFK(21) | 32 | 31 | 63 | >500 | 250 |
| 6 | FKA(2) | 33 | >500 | 125 | 16 | 500 |
| 12 | FKA(4) | 34 | >500 | 125 | 4 | 250 |
| 18 | FKA(6) | 35 | 8 | 8 | 4 | 500 |
| 21 | FKA(7) | 36 | 125 | 63 | 500 | 500 |
| 24 | FKA(8) | 37 | 125 | 16 | 8 | 125 |
| 27 | FKA(9) | 38 | 4 | 4 | 8 | 125 |
| 30 | FKA(10) | 39 | 8 | 16 | 8 | 8 |
| 51 | FKA(17) | 40 | 16 | 16 | 4 | 8 |
| 63 | FKA(21) | 41 | 8 | 16 | 4 | 125 |
| 4 | LK(2) | 42 | >500 | 250 | >500 | 16 |
| 10 | LK(5) | 43 | 62 | 62 | >500 | 31 |
| 14 | LK(7) | 60 | 8 | 8 | 16 | 4 |
| 16 | LK(8) | 44 | 8 | 16 | 31 | 4 |
| 18 | LK(9) | 45 | 8 | 8 | 16 | 4 |
| 20 | LK(10) | 46 | 8 | 8, 166 | 16 or less | 16 or less |
| 22 | LK(11) | 47 | 16 | 8 | 16 or less | 4 |
| 24 | LK(12) | 48 | 16 (3 log) | 4 | 4 | 8 |
| 36 | LK(18) | 49 | 16 | 31 | 8 | 16 |
| 48 | LK(24) | 50 | 16 | 63 | >500 | >500 |
| 14 | LR(7) | 51 | >63 | 4 | 31 | 7.8 |
| 18 | LR(9) | 52 | 31(3 log) | 4 | 16 | 8 |
| 22 | LR(11) | 53 | | 8 | 16 | 8 |
| 21 | KGK(7) | 64 | 500 | 500 | >500 | 500 |
| 33 | KGK(11) | 54 | 8 | 8 | >500 | 8 |
| 45 | KGK(15) | 55 | 4 | 16 | 125 | 62 |
| 21 | KTK(7) | 56 | 31 | 31 | 250 | 8 |

The results indicate that many of the periodic peptides have true biocidal activity. Surprisingly, even peptides too small to span the membrane demonstrate biocidal activity (FKA(2), FKA(4), LK(2), LK(4)). Therefore, the lower size limit for periodic peptides can in fact be as low as 4 residues.

EXAMPLE 6

Viral Testing

The prior experiments established bactericidal and fungicidal activity, as well as anti-tumor activity. The next prophetic experiments will establish antiviral activity.

Unique antimicrobial peptide D2A21, which has amino acid content similar to the peptides demonstrated herein, has been shown to have anti-bacterial, antifungal, anti-tumor and antiviral activity. Similarly, two well characterized natural antimicrobial peptides from insects—melittin and cecropin—have been shown to be effective against human immunodeficiency virus 1 (HIV-1), with IC50 values in the range 0.9–1.5 mM for melittin and 2–3 mM for cecropin (Wachinger (1998)). Therefore, we predict that a subset of the peptides described above will also have antiviral activity.

Antiviral activity can be measured in a number of ways, but one simple method of determining the effect on a retrovirus, such as HIV or FIV, is to measure decreased reverse transcriptase (RT) activity of a retrovirus and determine the 50% inhibitory concentration, which should be about 1 mM for effectiveness (Jia Ma (2002)).

All references cited herein are incorporated by reference in their entirety. The references are listed herein for convenience:
1. Durell S R, et al., *Modeling the ion channel structure of cecropin*, Biophys J. (1992 December) 63(6):1623–31.
2. E. Gazit, et al., *Interaction of the Mammalian Antibacterial Peptide Cecropin P1 with Phospholipid Vesicles*, Biochemistry (1995) 34, 11479.
3. Arlotti et al., *Efficacy of a synthetic lytic peptide in the treatment of prostate cancer*, Urol Oncol. (2001) 6(3): 97–102.
4. U.S. Pat. No. 5,789,542
5. Javadpour, et al., *De Novo Antimicrobial Peptides with Low Mammalian Cell Toxicity*, J. Med. Chem. (1996) 39(16): 3107–3113.
6. Wachinger, et al., *Antimicrobial peptides melittin and cecropin inhibit replication of human immunodeficiency virus 1 by suppressing viral gene expression*, J. Gen. Virol. (1998) (79): 731–740.
7. Jia Ma, et al., *Inhibitory Activity of Synthetic Peptide Antibiotics on Feline Immunodeficiency Virus Infectivity In Vitro*, J. Virol. (2002) 76(19): 9952–9961.
8. S. E. Blondelle and Karl Lohner, *Biopolymers (Peptide Science)*, (2000) Vol 55, 74–87.

What is claimed is:

1. A process for inhibiting growth of a target cell comprising administering to a target cell an antimicrobial peptide comprising a periodic peptide with repeating identical monomer units of 2, 3, or 4 residues, wherein the target cell is selected from the group consisting of bacteria, yeast, and fungi, and the antimicrobial peptide is administered in an amount effective to inhibit growth of said target cell, and wherein the periodic peptide is selected from the group consisting of Seq. ID. No. 1–23, 29–61, and 64.

2. The process of claim 1, wherein the periodic peptide is Seq. ID. No. 1.

3. The process of claim 1, wherein the periodic peptide is Seq. ID. No. 2.

4. The process of claim 1, wherein the periodic peptide is Seq. ID. No. 3.

5. The process of claim 1, wherein the periodic peptide is Seq. ID. No. 4.

6. The process of claim 1, wherein the periodic peptide is Seq. ID. No. 5.

7. The process of claim 1, wherein the periodic peptide is Seq. ID. No. 6.

8. The process of claim 1, wherein the periodic peptide is Seq. ID. No. 7.

9. The process of claim 1, wherein the periodic peptide is Seq. ID. No. 8.

10. The process of claim 1, wherein the periodic peptide is Seq. ID. No. 9.

11. The process of claim 1, wherein the periodic peptide is Seq. ID. No. 10.

12. The process of claim 1, wherein the periodic peptide is Seq. ID. No. 11.

13. The process of claim 1, wherein the periodic peptide is Seq. ID. No. 12.

14. The process of claim 1, wherein the periodic peptide is Seq. ID. No. 13.

15. The process of claim 1, wherein the periodic peptide is Seq. ID. No. 14.

16. The process of claim 1, wherein the periodic peptide is Seq. ID. No. 15.

17. The process of claim 1, wherein the periodic peptide is Seq. ID. No. 16.

18. The process of claim 1, wherein the periodic peptide is Seq. ID. No. 17.

19. The process of claim 1, wherein the periodic peptide is Seq. ID. No. 18.

20. The process of claim 1, wherein the periodic peptide is Seq. ID. No. 19.

21. The process of claim 1, wherein the periodic peptide is Seq. ID. No. 20.

22. The process of claim 1, wherein the periodic peptide is Seq. ID. No. 21.

23. The process of claim 1, wherein the periodic peptide is Seq. ID. No. 22.

24. The process of claim 1, wherein the periodic peptide is Seq. ID. No. 23.

25. The process of claim 1, wherein the periodic peptide is Seq. ID. No. 29.

26. The process of claim 1, wherein the periodic peptide is Seq. ID. No. 30.

27. The process of claim 1, wherein the periodic peptide is Seq. ID. No. 31.

28. The process of claim 1, wherein the periodic peptide is Seq. ID. No. 32.

29. The process of claim 1, wherein the periodic peptide is Seq. ID. No. 33.

30. The process of claim 1, wherein the periodic peptide is Seq. ID. No. 34.

31. The process of claim 1, wherein the periodic peptide is Seq. ID. No. 35.

32. The process of claim 1, wherein the periodic peptide is Seq. ID. No. 36.

33. The process of claim 1, wherein the periodic peptide is Seq. ID. No. 37.

34. The process of claim 1, wherein the periodic peptide is Seq. ID. No. 38.

35. The process of claim 1, wherein the periodic peptide is Seq. ID. No. 39.

36. The process of claim 1, wherein the periodic peptide is Seq. ID. No. 40.

37. The process of claim 1, wherein the periodic peptide is Seq. ID. No. 41.

38. The process of claim 1, wherein the periodic peptide is Seq. ID. No. 42.

39. The process of claim 1, wherein the periodic peptide is Seq. ID. No. 43.

40. The process of claim 1, wherein the periodic peptide is Seq. ID. No. 44.

41. The process of claim 1, wherein the periodic peptide is Seq. ID. No. 45.

42. The process of claim 1, wherein the periodic peptide is Seq. ID. No. 46.

43. The process of claim 1, wherein the periodic peptide is Seq. ID. No. 47.

44. The process of claim 1, wherein the periodic peptide is Seq. ID. No. 48.

45. The process of claim 1, wherein the periodic peptide is Seq. ID. No. 49.

46. The process of claim 1, wherein the periodic peptide is Seq. ID. No. 50.

47. The process of claim 1, wherein the periodic peptide is Seq. ID. No. 51.

48. The process of claim 1, wherein the periodic peptide is Seq. ID. No. 52.

49. The process of claim 1, wherein the periodic peptide is Seq. ID. No. 53.

50. The process of claim 1, wherein the periodic peptide is Seq. ID. No. 54.

51. The process of claim 1, wherein the periodic peptide is Seq. ID. No. 55.

52. The process of claim 1, wherein the periodic peptide is Seq. ID. No. 56.

53. The process of claim 1, wherein the periodic peptide is Seq. ID. No. 57.

54. The process of claim 1, wherein the periodic peptide is Seq. ID. No. 58.

55. The process of claim 1, wherein the periodic peptide is Seq. ID. No. 59.

56. The process of claim 1, wherein the periodic peptide is Seq. ID. No. 60.

57. The process of claim 1, wherein the periodic peptide is Seq. ID. No. 61.

58. The process of claim 1, wherein the periodic peptide is Seq. ID. No. 64.

59. A process for killing a target cell comprising administering to a target cell an antimicrobial peptide comprising a periodic peptide with repeating identical monomer units of 2, 3, or 4 residues, wherein the target cell is selected from the group consisting of bacteria, yeast, and fungi, and the antimicrobial peptide is administered in an amount effective to kill said target cell, and wherein the periodic peptide is selected from the group consisting of Seq. ID. No. 1–23, 29–61, and 64.

60. The process of claim 59, wherein the periodic peptide is Seq. ID. No. 1.

61. The process of claim 59, wherein the periodic peptide is Seq. ID. No. 2.

62. The process of claim 59, wherein the periodic peptide is Seq. ID. No. 3.

63. The process of claim 59, wherein the periodic peptide is Seq. ID. No. 4.

64. The process of claim 59, wherein the periodic peptide is Seq. ID. No. 5.

65. The process of claim 59, wherein the periodic peptide is Seq. ID. No. 6.

66. The process of claim 59, wherein the periodic peptide is Seq. ID. No. 7.

67. The process of claim 59, wherein the periodic peptide is Seq. ID. No. 8.

68. The process of claim 59, wherein the periodic peptide is Seq. ID. No. 9.

69. The process of claim 59, wherein the periodic peptide is Seq. ID. No. 10.

70. The process of claim 59, wherein the periodic peptide is Seq. ID. No. 11.

71. The process of claim 59, wherein the periodic peptide is Seq. ID. No. 12.

72. The process of claim 59, wherein the periodic peptide is Seq. ID. No. 13.

73. The process of claim 59, wherein the periodic peptide is Seq. ID. No. 14.

74. The process of claim 59, wherein the periodic peptide is Seq. ID. No. 15.

75. The process of claim 59, wherein the periodic peptide is Seq. ID. No. 16.

76. The process of claim 59, wherein the periodic peptide is Seq. ID. No. 17.

77. The process of claim 59, wherein the periodic peptide is Seq. ID. No. 18.

78. The process of claim 59, wherein the periodic peptide is Seq. ID. No. 19.

79. The process of claim 59, wherein the periodic peptide is Seq. ID. No. 20.

80. The process of claim 59, wherein the periodic peptide is Seq. ID. No. 21.

81. The process of claim 59, wherein the periodic peptide is Seq. ID. No. 22.

82. The process of claim 59, wherein the periodic peptide is Seq. ID. No. 23.

83. The process of claim 59, wherein the periodic peptide is Seq. ID. No. 29.

84. The process of claim 59, wherein the periodic peptide is Seq. ID. No. 30.

85. The process of claim 59, wherein the periodic peptide is Seq. ID. No. 31.

86. The process of claim 59, wherein the periodic peptide is Seq. ID. No. 32.

87. The process of claim 59, wherein the periodic peptide is Seq. ID. No. 33.

88. The process of claim 59, wherein the periodic peptide is Seq. ID. No. 34.

89. The process of claim 59, wherein the periodic peptide is Seq. ID. No. 35.

90. The process of claim 59, wherein the periodic peptide is Seq. ID. No. 36.

91. The process of claim 59, wherein the periodic peptide is Seq. ID. No. 37.

92. The process of claim 59, wherein the periodic peptide is Seq. ID. No. 38.

93. The process of claim 59, wherein the periodic peptide is Seq. ID. No. 39.

94. The process of claim 59, wherein the periodic peptide is Seq. ID. No. 40.

95. The process of claim 59, wherein the periodic peptide is Seq. ID. No. 41.

96. The process of claim 59, wherein the periodic peptide is Seq. ID. No. 42.

97. The process of claim 59, wherein the periodic peptide is Seq. ID. No. 43.

98. The process of claim 59, wherein the periodic peptide is Seq. ID. No. 44.

99. The process of claim 59, wherein the periodic peptide is Seq. ID. No. 45.

100. The process of claim 59, wherein the periodic peptide is Seq. ID. No. 46.

101. The process of claim 59, wherein the periodic peptide is Seq. ID. No. 47.

102. The process of claim 59, wherein the periodic peptide is Seq. ID. No. 48.

103. The process of claim 59, wherein the periodic peptide is Seq. ID. No. 49.

104. The process of claim 59, wherein the periodic peptide is Seq. ID. No. 50.

105. The process of claim 59, wherein the periodic peptide is Seq. ID. No. 51.

106. The process of claim 59, wherein the periodic peptide is Seq. ID. No. 52.

107. The process of claim 59, wherein the periodic peptide is Seq. ID. No. 53.

108. The process of claim 59, wherein the periodic peptide is Seq. ID. No. 54.

109. The process of claim 59, wherein the periodic peptide is Seq. ID. No. 55.

110. The process of claim 59, wherein the periodic peptide is Seq. ID. No. 56.

111. The process of claim 59, wherein the periodic peptide is Seq. ID. No. 57.

112. The process of claim 59, wherein the periodic peptide is Seq. ID. No. 58.

113. The process of claim 59, wherein the periodic peptide is Seq. ID. No. 59.

114. The process of claim 59, wherein the periodic peptide is Seq. ID. No. 60.

115. The process of claim 59, wherein the periodic peptide is Seq. ID. No. 61.

116. The process of claim 59, wherein the periodic peptide is Seq. ID. No. 64.

* * * * *